US010213365B1

(12) United States Patent
Sukkarieh

(10) Patent No.: US 10,213,365 B1
(45) Date of Patent: Feb. 26, 2019

(54) DOSE INDICATION DEVICE

(71) Applicant: Zafer Sukkarieh, Bemidji, MN (US)

(72) Inventor: Zafer Sukkarieh, Bemidji, MN (US)

( * ) Notice: Subject to any disclaimer, the term of this patent is extended or adjusted under 35 U.S.C. 154(b) by 196 days.

(21) Appl. No.: 15/218,634

(22) Filed: Jul. 25, 2016

Related U.S. Application Data

(60) Provisional application No. 62/197,766, filed on Jul. 28, 2015, provisional application No. 62/222,378, filed on Sep. 23, 2015.

(51) Int. Cl.

| | |
|---|---|
| ***A61B 19/00*** | (2006.01) |
| ***A61J 1/18*** | (2006.01) |
| ***A61J 1/14*** | (2006.01) |
| ***A61J 7/04*** | (2006.01) |

(52) U.S. Cl.
CPC ............... *A61J 1/18* (2013.01); *A61J 1/1412* (2013.01); *A61J 7/04* (2013.01); *A61J 2200/30* (2013.01); *A61J 2205/30* (2013.01); *A61J 2205/50* (2013.01)

(58) Field of Classification Search
CPC .... A61J 1/18; A61J 1/1412; A61J 7/04; G09F 11/23; G09F 11/04
See application file for complete search history.

(56) References Cited

U.S. PATENT DOCUMENTS

| | | | |
|---|---|---|---|
| 5,694,882 A | 12/1997 | Marshall | |
| 6,003,467 A | 12/1999 | Shelton-Ferrell et al. | |
| 6,152,067 A | 11/2000 | Mathison | |
| 6,789,497 B1 | 9/2004 | Aiken | |
| 7,314,022 B2 | 1/2008 | Sollaccio | |
| 7,556,151 B2 | 7/2009 | Siejas | |
| 7,779,775 B2 * | 8/2010 | Campbell | G04C 23/08 116/300 |
| 9,021,980 B1 | 5/2015 | Vasta et al. | |
| 9,021,981 B2 | 5/2015 | Raiti de Boyles | |
| 9,084,594 B2 | 7/2015 | Suh et al. | |
| 2003/0192468 A1 | 10/2003 | Goertzen | |
| 2007/0056503 A1 * | 3/2007 | Sollaccio | G09F 11/23 116/308 |
| 2008/0257851 A1 * | 10/2008 | Vargas | A61J 7/04 215/230 |
| 2009/0159544 A1 * | 6/2009 | Tune | B65D 1/0223 211/153 |
| 2009/0293798 A1 | 12/2009 | Kreshek | |

(Continued)

*Primary Examiner* — Ariana Zimbouski

(74) *Attorney, Agent, or Firm* — Charles S. Sara; DeWitt LLP

(57) ABSTRACT

A record-keeping indicator device, and in particular, to an indicator device associated with medicine containers permits a user to determine the number of doses of medicine taken in a successive interval and on a given day. The indicator device includes a disk having a top and bottom surface. The top surface displays a first set of indicia for the seven days of the week spaced circumferentially around the perimeter. A second set of indicia for the number of doses of medication ingested are evenly spaced between each indicator of the first set. A dial or arrow arm, at the center of the disk, extends outwardly toward the dose indicia and is rotatable about the disk via a turning mechanism. The bottom surface of the disk contains an adhesive material which allows the disk to be attached to any surface of a medicine container.

16 Claims, 8 Drawing Sheets

(56) References Cited

U.S. PATENT DOCUMENTS

2012/0006252 A1* 1/2012 Warner .................. G09F 11/23
116/284
2015/0078139 A1* 3/2015 Raiti de Boyles ........ A61J 7/04
368/10

* cited by examiner

DOSE INDICATION DEVICE

CROSS-REFERENCE TO RELATED APPLICATION

The application claims priority to U.S. Provisional Application entitled "Timely Dose Pill Reminder Indication Device," Ser. No. 62/197,766, filed Jul. 28, 2015, and U.S. Provisional Application entitled "Timely Dose Pill Reminder Indication Device," Ser. No. 62/222,378, filed Sep. 23, 2015, both of which are incorporated herein by reference in its entirety.

BIBLIOGRAPHY

Complete bibliographical citations to the documents cited herein can be found in the Bibliography, immediately preceding the claims.

FIELD OF THE INVENTION

The present invention is directed to a reminder or indicator device and, more particularly, to a dose reminder device designed to assist users to record the intake of pills and other medications in order to prevent missing a required dose or to prevent and unintended overdose. The indicator device is intended to be placed, either permanently or temporarily, on bottles and other containers or their tops, boxes, and metal or other surfaces.

BACKGROUND

Many Americans and the world population at large use prescription or over the counter drugs as well as vitamins and supplements at an increasing rate. In most cases these medications require strict instructions. With an aging population, reduced dexterity, impaired vision and the stress of everyday living, the dangers of a missing dose or overdose are very real. Some medications must be taken daily and at multiple intervals, while others only as needed. It is important for the patient or the caregiver to know when the last dose was taken to prevent an overdose. Losing track of the required medication regimen may result in a missed dose or an overdose, both of which can be dangerous to the patient's health. One study estimated that the elderly observe a 50% adherence to proper dose. That is translated into a 300 billion dollar problem. Serious illness or even death are also major concerns (Basca 2008).

There are a variety of attempted solutions, including pill cases, alarm devices, lists and reminder devices. With respect to pill cases, there are a myriad of different boxes and shapes divided into small containers or dividers to store pills for daily, weekly or monthly use. The pill containers can also come equipped with alarms. However, in most cases, costs and complexities make their appeal limited.

The prior art also includes patents relating to this technology. For example, U.S. Pat. No. 5,694,882 to Marshall relates to an indicator and more particularly to a mechanism permitting a patient to determine the number of doses of medicine taken or remaining to be ingested in a designated interval. The dose indicator is a molded plastic disk to which an indicator arm is connected. Affixed to the underside of the disk is a pressure-sensitive adhesive, allowing the disk to be attached to at least one surface of existing commercial medicine containers. Embossed on the upper surface of a disk are indicia, typically numbers corresponding to doses of medicine. Additionally protruding above the upper surface are two pins or other projections which limit travel or placement of the indicator arm. One pin, whose location may be fixed for all disks, prevents the patient from attempting to place the arm outside its intended range of travel. The location of the other pin may vary, however, depending on the number of doses of medication the patient is prescribed in a particular interval.

U.S. Pat. No. 6,789,497 to Aiken discloses an indicator or numbering device for keeping track of the number of vitamins/medicine pills that one has taken. The invention comprises a circular cover disk having a circular base plate disposed therein, along with an indicator disposed between the cover disk and the base plate. The cover disk has an aperture therein which permits viewing of the days of the week which are stamped onto the top of the circular base plate. The indicator operates rotatably between the cover disk and the base plate to indicate the number of medications taken on a given day. The circular base plate may be attached to the top of a medicine bottle via a two-sided, adhesive strip.

U.S. Pat. No. 9,021,980 to Vasta and Rosenblum is directed to a dosage indicator assembly comprising a dosage display panel, a day display panel and a pointer. The pointer is selectively movable into and out of a plurality of predetermined positions relative to the dosage display panel and is structured to selectively align with or point to one or more dosage indicia disposed on the dosage display panel. The day indicia may be selectively disposed or visible through a display window, opening and/or aperture where a user can set or select the day.

U.S. Pat. No. 9,021,981 to Raiti de Boyles is directed to a device to be mounted or adhere to a bottle cap, a box or other surface that tracks when the last day and dose of a medicine was taken or when the next is due. The invention comprises two disk and a dial. The base disk has indicia representing the days of the week, and a central pin protruding from the center that clasp the three elements together. The cover disk has indicia for the dose and a window to see the indicia of the base disk. The dial points to the dose indicia and holds the three components together once the pin from the base disk clasp inside its aperture.

U.S. Pat. No. 7,314,022 to Sollaccio is directed to a medicine bottle cap with time and day markers and includes a main cap member, a first set of indicia, a second set of indicia, a central axle, a first arrow arm and a second arrow arm. Both sets of indicia are in a circular pattern located on the top of the cap. The first set of indicia is a fourteen position set of indicia, seven of which represent ante meridiem and each of the seven days of the week, and seven of which represent post meridiem and each of the seven days of the week. A central axle holds a rotatable first arrow arm that extends to the first set of indicia, and a second arrow arm that extends to the second set of indicia.

U.S. Patent Publication 2003/0192468 to Goertzen is directed to an elastic O-ring or other expandable type ring indicator is disclosed that has indicia around its periphery identifying time, day, date or dose intervals. The ring is secured around either a cap or a neck of a conventional medicine or pill bottle. The cap or neck is provided with a pointer. The user then rotates the cap relative to the container to line up the pointer with the appropriate indicia on the ring. In another embodiment the user rotates the O-ring relative to the container or the cap to line up the pointer with the appropriate indicia on the ring. The ring is reusable and fits on conventional containers and caps.

U.S. Pat. No. 7,556,151 to Seijas is directed to a reminder device that can be attached to the bottom of a medicine container that has a cap. The reminder device has an indicator rotatably mounted on a base in order to rotate and indicate a scheduled event. The base adhesively or frictionally engages the bottom of the container opposite the cap. The base may have an opening for engaging the bottom of the medicine container. Along some transverse plane within the opening, the opening may be shaped to engage the container along most of its periphery. A user can adjust the indicator on the base to indicate a scheduled event when medicine is ingested.

U.S. Pat. No. 8,074,594 to Lu is directed to an indicating device suitable for indicating a number of metered dosages of a substance that have been dispensed from or remain in a container. The indicating device includes at least one primary indicator member having primary dosage indicia, configured as numeric indicia, and a second indicator member having secondary dosage indicia, configured with at least two different colors. The primary and secondary indicator members are coaxially mounted. In one embodiment, a device for dispensing dosages of the substance also includes a dispenser housing and a container.

However, most of the prior art devices are complicated with multiple moving parts making them difficult to use. Therefore, there is a need for a reliable, inexpensive and disposable reminder device to aid in reminding patient either when a dose was administered or of the intervals at which they are due to ingest specific dosages of medicine.

SUMMARY OF THE INVENTION

With reference to the attached figures for the reference numbers, the present relates to record-keeping indicator devices, and in particular, to an indicator device 10 associated with medicine containers which permits a user to determine the number of doses of medicine taken in a successive interval and on a given day. The indicator device 10 features a base disk 40 having a first upper surface 42 and a second lower surface 48. The first upper surface 42 displays a first set of indicia 54 for the seven days of the week spaced circumferentially around the perimeter of the first upper surface 42. A second set of indicia for the number of doses of medication ingested are evenly spaced between each indicator of the first set of indicia. A rotating reminder dial 60, at the center 46 of the base disk 40, extends outwardly toward the dose indicia 54 and is rotatable about the base disk 40 via a turning mechanism. The second lower surface 48 of the base disk 40 contains an adhesive material 80 which allows the base disk 40 to be attached to any surface of a medicine container 12.

In particular, the present invention is directed to a dose indicator device 10 for attachment to a container cap 14 on a container 12, comprising a base disk 40 having a first upper surface 42 and a second lower surface 48 where in the first upper surface 42 includes a center mount axle 44 extending from center 46 of the first upper surface 42 of the base disk 40, wherein the axle 44 includes a shaft 50 and a head 52 and wherein the head 52 is slightly larger in circumference to the shaft 50, wherein the first upper surface 42 displays dose indicia 54 for indicating time and the second lower surface 48 of the base disk 40 contains an adhesive material 80 which allows the base disk 40 to be attached to a surface, and a reminder dial 60 rotatably positioned at the center 46 of the base disk 40 by means of the axle 44 and extending outwardly toward the dose indicia 54.

The present invention is further directed to a container cap 140 for attachment to a container 12, the container cap 140 including a dose indicator device 100, the container cap 140 comprising a first upper surface 124 with a closure wall 128 and a container closure mechanism located on the interior of the closure wall 128, wherein the first upper surface 124 includes a center mount axle 144 extending from center 146 of the first upper surface 124, wherein the axle 144 includes a shaft 150 and a head 152 and wherein the head 152 is slightly larger in circumference to the shaft 150, wherein the first upper surface 124 displays dose indicia 54 for indicating time; and a reminder dial 160 rotatably affixed to the axle 144, wherein the reminder dial 160 includes an indicator pointer 174 extending outwardly toward the dose indicia 54.

The present invention is further directed to a dose indicator device 10 for attachment to a container 12, wherein the container 12 includes an open, upper first end 16, a closed, bottom second end 18 and a sidewall 20, the dose indicator device 10 comprising a base disk 40 including a first upper surface 42 and a second lower surface 48 wherein the first upper surface 42 includes a center mount axle 44 extending from center 46 of the first upper surface 42 of the base disk 40, wherein the axle 44 includes a shaft 50 and a head 52 and wherein the head 52 is slightly larger in circumference to the shaft 50, and wherein the first upper surface 42 displays dose indicia 54 for indicating time and the second lower surface 48 of the base disk 40 contains an adhesive material 80 which allows the base disk 40 to be attached to a surface; a reminder dial 60 rotatably positioned at the center 46 of the base disk 40 by means of the axle 44 and extending outwardly toward the dose indicia 54; and a securing strap 204 including a flat surface 202 for receiving the second lower surface 48 of the base disk 40 of the dose indicator device 10; wherein the securing strap secures the dose indicator device 10 to the sidewall 20 of the container 12.

Advantageously, the present invention is a cost effective and useful system to produce and use. By use of the dose indicator device 10 of the present invention, the safety and integrity of medications are preserved and the dose intervals of medications are assured.

With the dose indicator device 10 of the present invention, simplicity and ease of use are unmatched. There is only one moving part: the rotating reminder dial 60. No elderly person should have the slightest difficulty in seeing or using this invention. The dose reminders are clear and easily readable, and no batteries are used that can cause device malfunction or fading of display.

The mechanism involved is durable and reliable. Prescription bottles may be carried in purses or pockets without any impact on reliability or condition.

The versatility of the dose indicator device 10 is unmatched in terms of applicability and visibility. It could be attached to a bottle top, side or to any surface. It meets any dose requirements such as pills or liquid once or three times a day with or without meals. Every four or six hours. Erasable instructions add to its versatility.

The indicator device 10 of the present invention shows the day and the dose of the medication was taken. Some prescriptions require that medications be taken 1, 2 or 3 or more times a day. In one embodiment, the indicator device 10 of the present invention records a maximum of three intervals per day.

The dose indicator device 10 can be attached to any medicine container 12 using a self-adhesive 80 or a securing strap 203 around the container 12. Alternatively, the dose indicator device 100 can be integrated with the container cap 120.

The objects and advantages of the invention will appear more fully from the following detailed description of the preferred embodiment of the invention made in conjunction with the accompanying drawings.

DETAILED DESCRIPTION OF THE INVENTION

Figure 1:
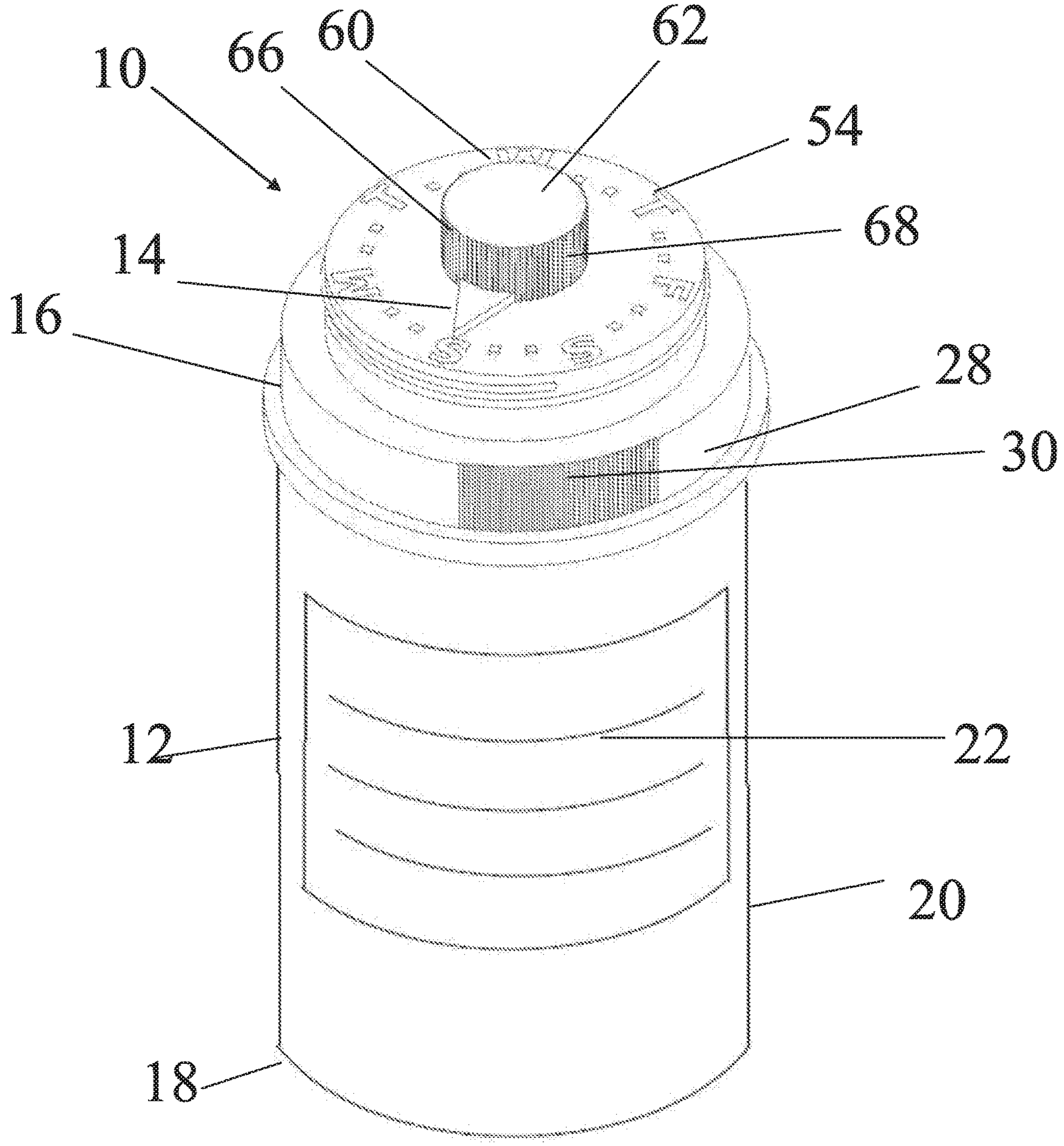
FIG. 1 is a perspective view of a medicine pill container including the indicator device of the present invention.

With reference to the figures, and specifically to FIGS. 1-5, the present invention is directed to a dose indicator device 10 and method to allow a user to track medication dosage times. While the present invention is specifically directed to medication dosage, it is within the scope of this invention to apply the indicator device 10 of the present invention to other uses and to other industries needing reminder times.

The indicator device 10 of the present invention is designed to easily attach to any type of container 12, whether flexible or rigid, or box or a container cap 14.

In a first embodiment, the indicator device 10 can be removable or permanently affixed to the top of a container cap 14. The container cap 14 will be used to temporarily seal a medicine container 12, pill bottle or the like.

The bottle or container 12 typically has an open, upper first end 16, a closed, bottom second end 18 and a generally cylindrical sidewall 20. The first end 16 includes a mechanism for closing the container cap 14 onto the container 12 (not illustrated). Such mechanism includes threading or a snap bead or the like for receiving the container cap 14. The bottom end 18 is generally flat for allowing the container 12 to stand in an upright position.

A prescription label 22, which identifies the patient, the medicine and the dosage, is typically adhered to the sidewall 20.

The container cap 14 includes a top surface 24 with a circular side wall 26 and a container closure wall 28 with threading located on the interior of the container closure wall 28 (not illustrated).

The container cap 14 may be child resistant or not child resistant. The container cap 14 may also be a standalone cap for retrofitting over existing caps.

The container cap 14 may be knurled with ridges 30 on the container closure wall 28 to assist with gripping the container cap 14 for opening and closing the container cap 14 over the container 12.

Figure 3:
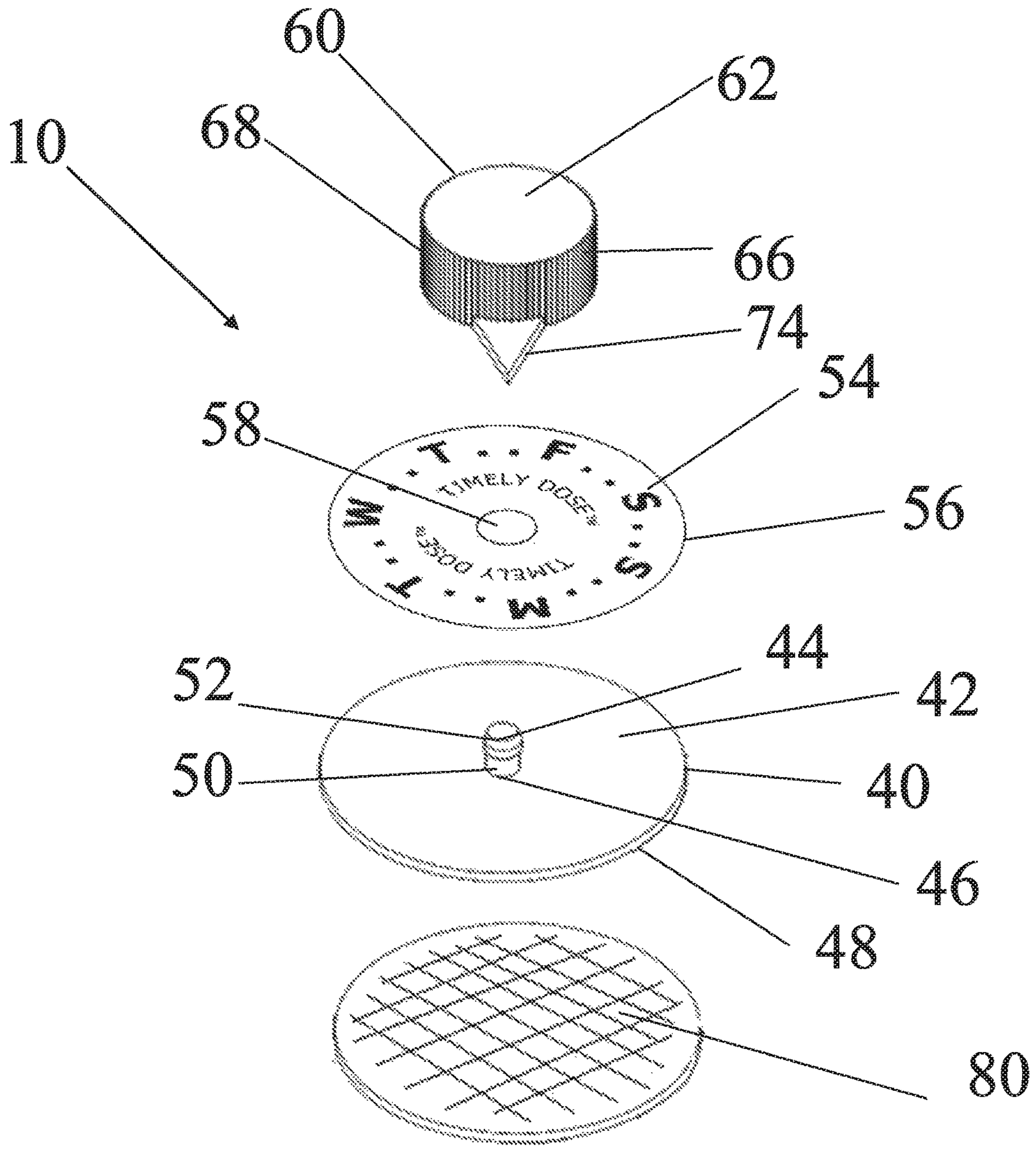
FIG. 3 is an exploded perspective view of the indicator device of FIG. 1.

As illustrated best in FIG. 3, the indicator device 10 includes a base disk 40, which is generally a circular platform having a first upper surface 42 with a center mount pin or axle 44 extending from center 46 of the first upper surface 42 of the base disk 40 and a second lower surface 48. The axle 44 includes a shaft 50 and a head 52. The head 52 is slightly larger in circumference to the shaft 50 on the axle 44.

Figure 2:
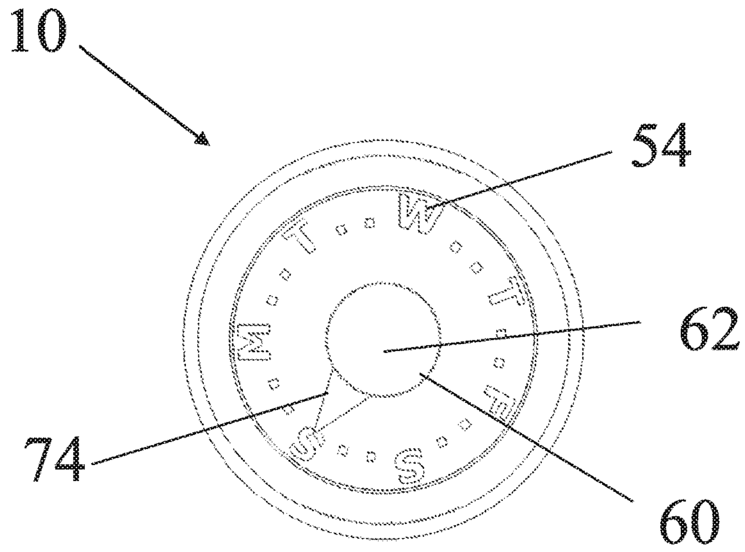
FIG. 2 is a top plan view of the indicator device of the present invention.
Figure 4:
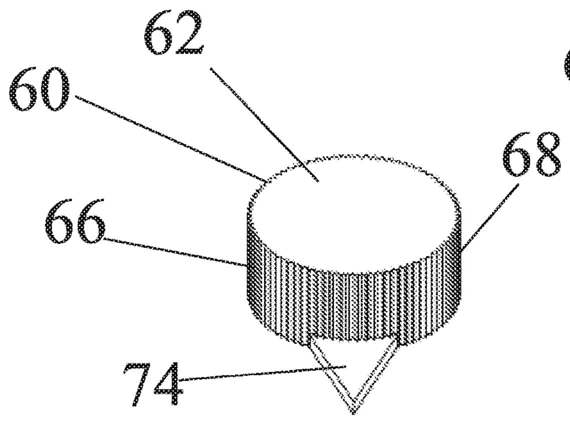
FIG. 4 is a top perspective view of the rotating reminder dial of the present invention.

The first upper surface 42 of the base disk 40 can include indicia 54 printed directly thereon, as illustrated in FIGS. 1 and 2, for determining when a medication must be taken. Alternatively and as illustrated in FIG. 3, the indicia 54 can be printed on a separate plastic or paper overlay plate 56 which is adhered to the first upper surface 42 of the base disk 40. The overlay plate 56 is cut in generally the same shape as the first upper surface 42 of the base disk 40 and includes a centrally space aperture 58 to receive the center mount axle 44. The indicia 54 may be any indicia that connote time. As illustrated the indicia 54 can indicate the days of the week and intervals within a day. Other types of indicia are of course contemplated.

Figure 5:
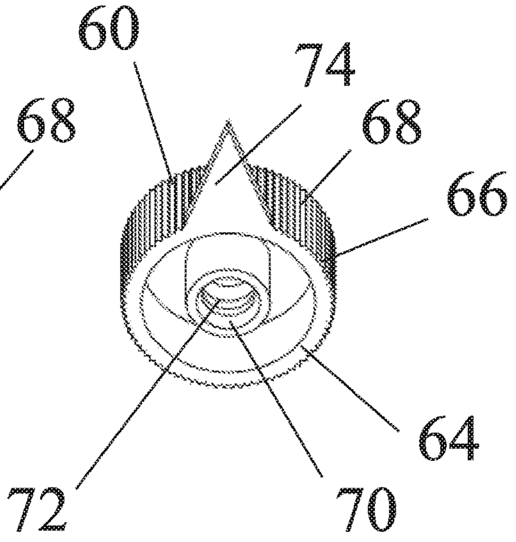
FIG. 5 is a bottom perspective view of the rotating reminder dial of the present invention.

Situated on the base disk 40 is a rotating reminder dial 60 which is rotatably connected to the base disk 40 by means of the center mount axle 44. The reminder dial 60 includes a first top end 62, a second bottom end 64, illustrated best in FIG. 5, and a generally circular side wall 66 disposed therebetween. The circular side wall 66 can include ridges 68 to assist the operator in turning the dial 60. As illustrated in FIG. 5, the second bottom end 64 of rotating reminder dial 60 includes a cylindrical aperture 70 for rotatably receiving the center mount axle 44 of the base disk 40. The cylindrical aperture 70 includes an internal ring 72 approximately midway through the cylindrical aperture 70. The purpose of the ring 72 is to retain the head 52 of the axle 44 when the rotating dial 60 is press fit onto the axle 44. In this manner the rotating dial 60 will remain rotatably connected to the axle 44 of the base disk 40 until it is forcibly removed. The rotating dial 60 rotates around the base disk 40 using the axle 44 as an axis.

The first top end 62 of the rotating dial 60 can be blank, as illustrated, to receive writings. For example, the name of the person receiving the medication or the name of the medication can be placed on the first top end 62. The ink can be removable for multiple use.

The rotating dial 60 includes a pointer or indicator arrow 74 to indicate the direction pointed and to work with the indicia 54 in order to designate the medication time.

The indicator device 10 can be temporarily affixed to the container cap by glue, adhesive, VELCRO® fasteners, or the like. The indicator device 10 can work equally well with a magnet base instead of a glue or adhesive base for placement on a metal board, refrigerator wall or the like. In addition a double adhesive side backing 80, illustrated in FIGS. 3 and 7, may be used to adhere the indicator device 10 to the top surface 24 of the container cap 14. The self-adhesive backing 80 may be made of plastic or paper, with plastic material being preferred.

One side of the self-adhesive backing 80 may be covered with a commercial grade glue such as those found on band aids or stickers, and again covered with a peelable paper, thus allowing the user to peel the paper off of the backing 80 and, using the glue side, attach the indicator device 10 to the upper surface 24 of the container cap 14. Flexible plastic is the preferred backing material.

Figure 6:
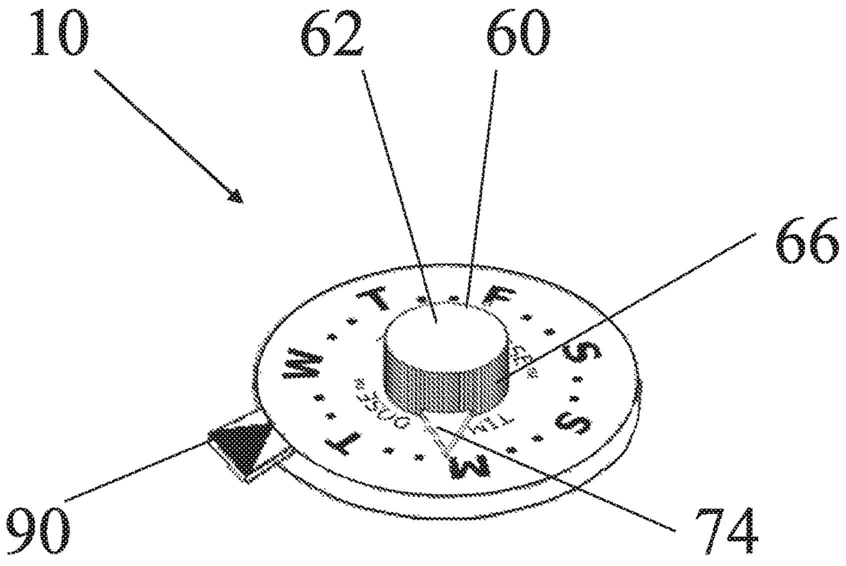
FIG. 6 is a top perspective view of a first alternative embodiment of the indicator device of the present invention.
Figure 7:
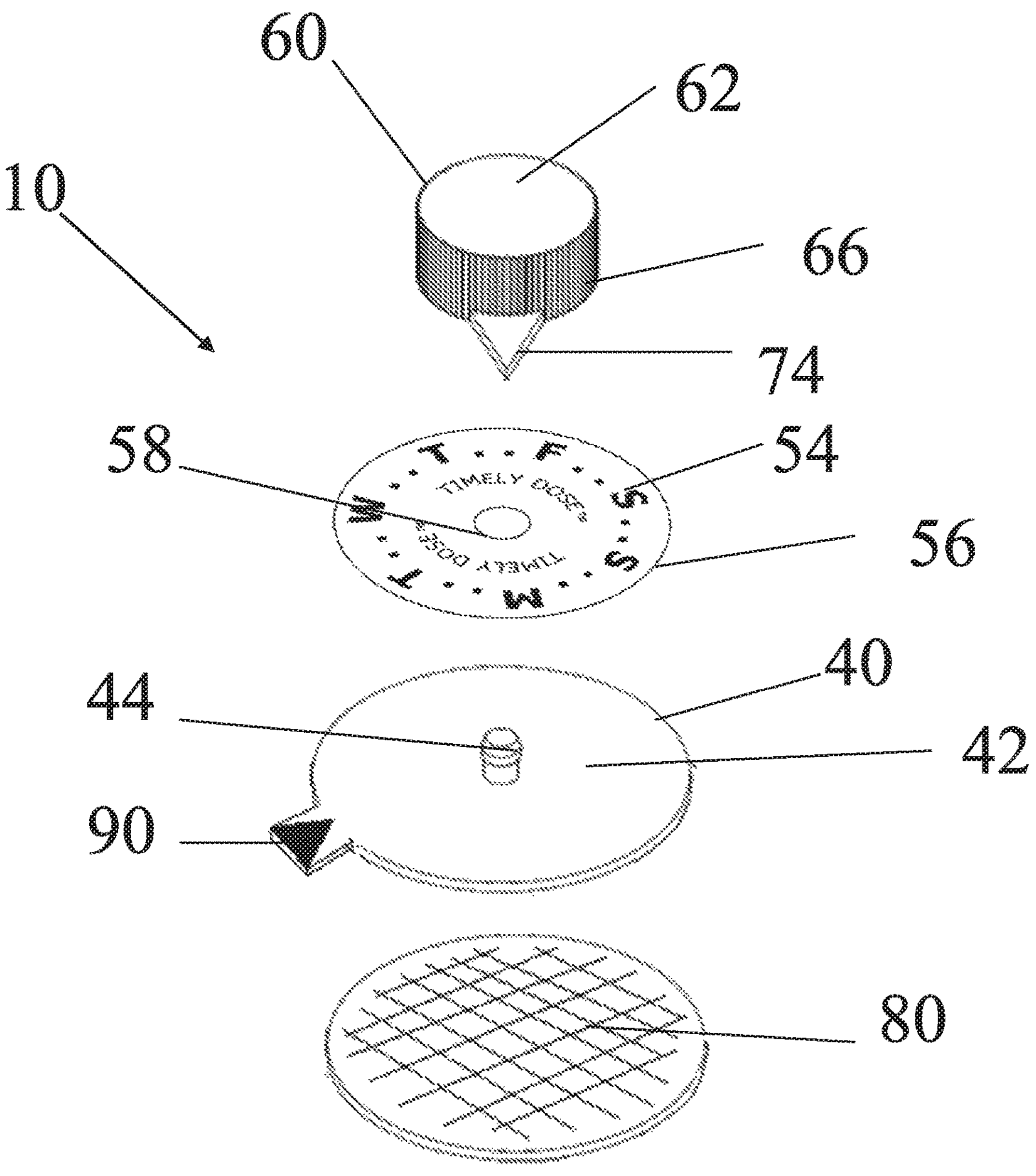
FIG. 7 is an exploded perspective view of the indicator device of FIG. 6.

Referring to FIGS. 6 and 7, the base disk 40 can include a second pointer 90 for designating a second date/time of interest. In this manner, the base disk 40 is adhered to the upper surface 24 of the container cap 14. The second pointer 90 may be adhered to the base disk 40 or the second pointer 90 may be formed as part of the base disk 40, as illustrated in FIG. 7. A rotating indicia plate 56 with the center-spaced aperture 58 is then placed over the base disk 40 such that the opening 58 is placed over the axle 44. The rotating dial 60 is then snap fit onto the base disk 40 as described above. In this manner the rotating indicia plate 56 can rotate to coordinate its indicia with the second pointer 90. The rotating dial 60 can then rotate with respect to a second indicia point on the indicia plate 56.

Figure 8:
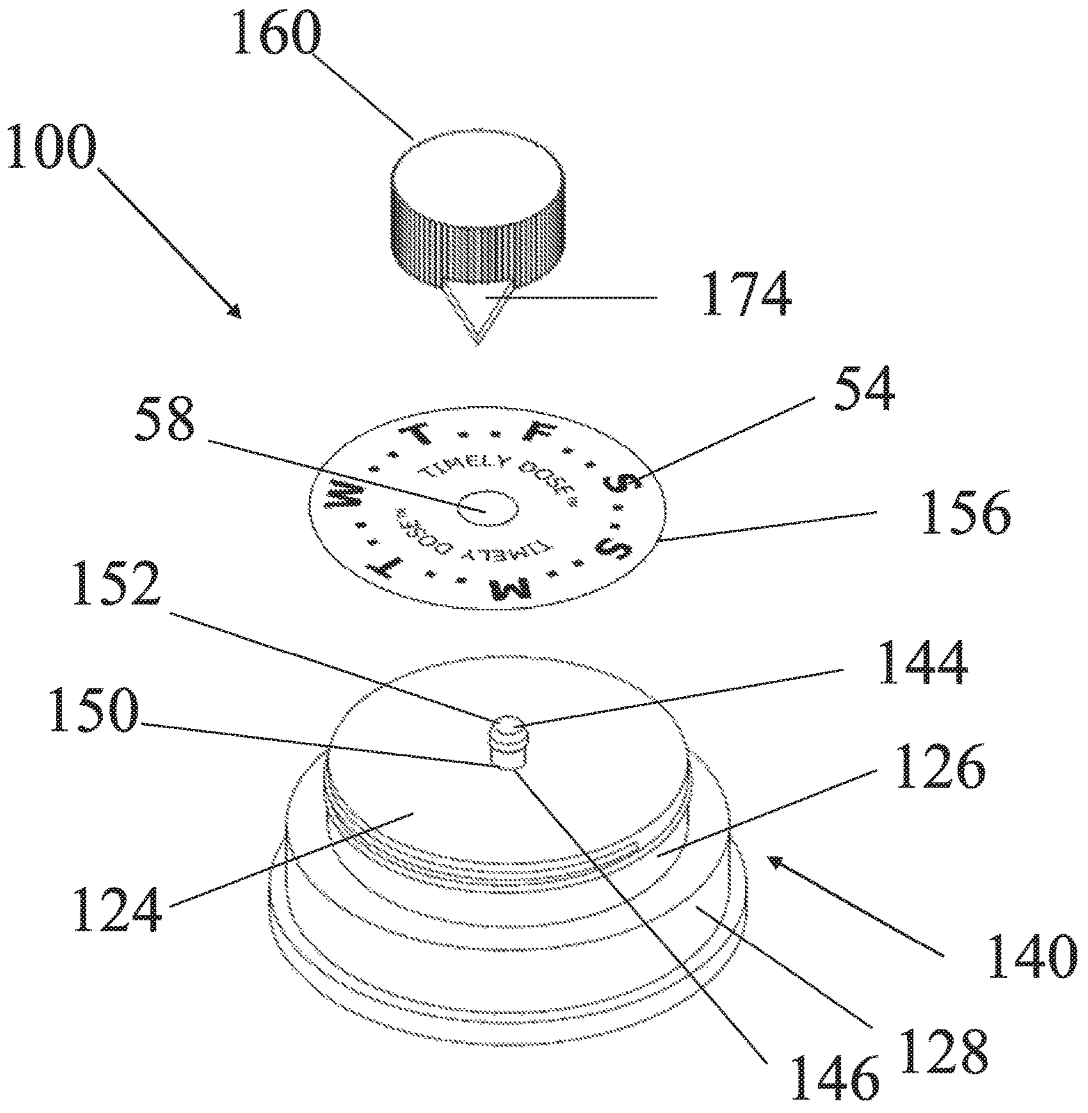
FIG. 8 is an exploded view of a second alternative embodiment of the indicator device of the present invention.

Referring to FIG. 8 for a second embodiment of a dose indicator device 100, there is illustrated a container cap 140 for attachment to a standard container 12, such as that illustrated in FIG. 1. The container cap 140 includes the dose indicator device 100 attached directly to the first upper surface 124 of the container cap 120. The container cap 140 is defined by the first upper surface 124 with a circular side wall 126, a container closure wall 128 and an interior container closure mechanism (not illustrated) located on the interior of the container closure wall 128 for sealing the container cap 120 to the container 12. The first upper surface 124 includes a center mount axle 144 extending from center 146 of the first upper surface 124 of the container cap 140. As with the device illustrated in FIGS. 1-3, the axle 144 includes a shaft 150 and a head 152 wherein the head 152 is slightly larger in circumference to the shaft 150 to accommodate the rotating reminder dial 60. The first upper surface 124 can display dose indicia directly on the upper surface, similar to that shown in FIGS. 1-2, for indicating time. Alternatively, an overlay plate 156, similar to the plate 56 in FIGS. 3 and 5, can be used. A reminder dial 160, such as that described with respect to FIGS. 1-7, is rotatably affixed to the axle 144. The reminder dial 160 includes an indicator pointer 174 extending outwardly toward the dose indicia 54. The characteristics of the reminder dial 160 are the same as that described with respect to FIGS. 1-7.

Figure 9:
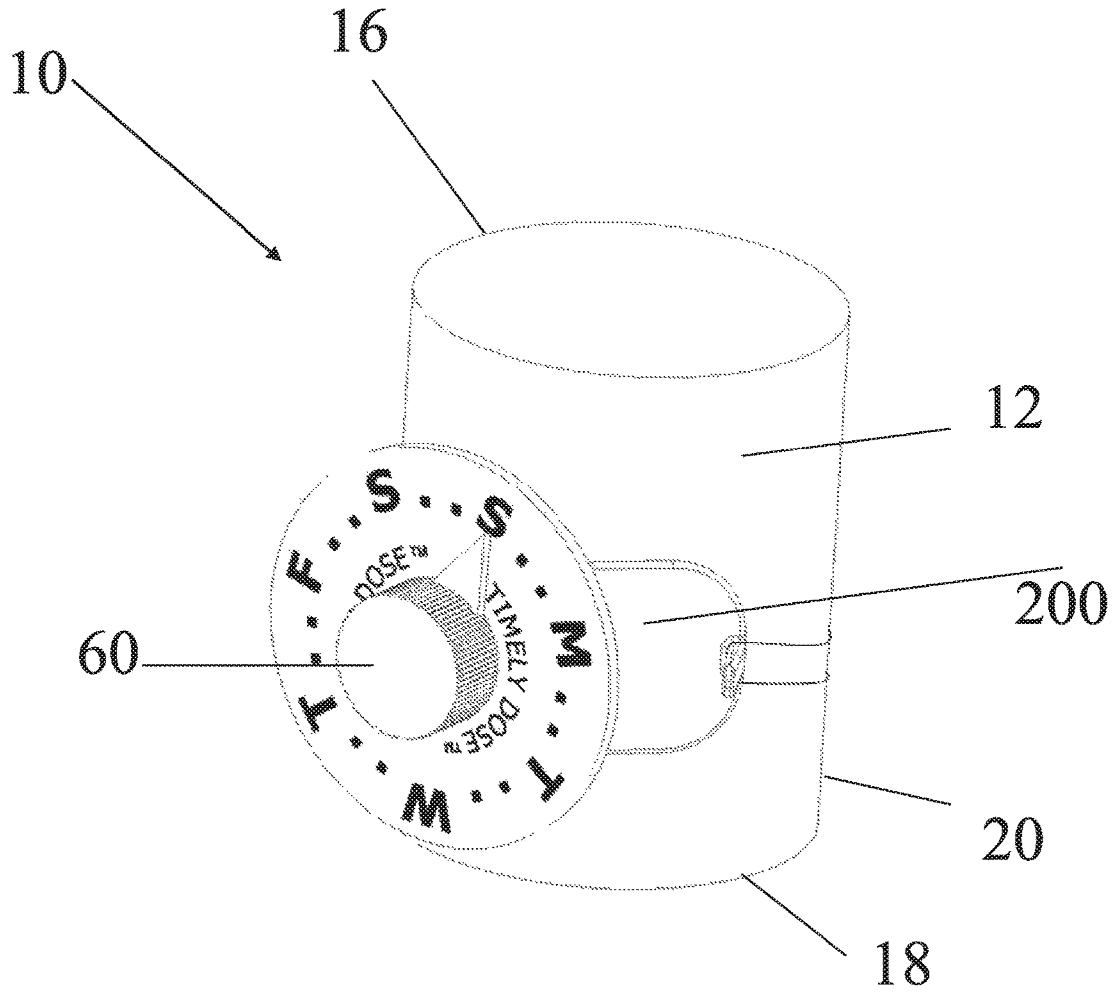
FIG. 9 is a perspective of a third embodiment of the indicator device of the present invention.
Figure 10:
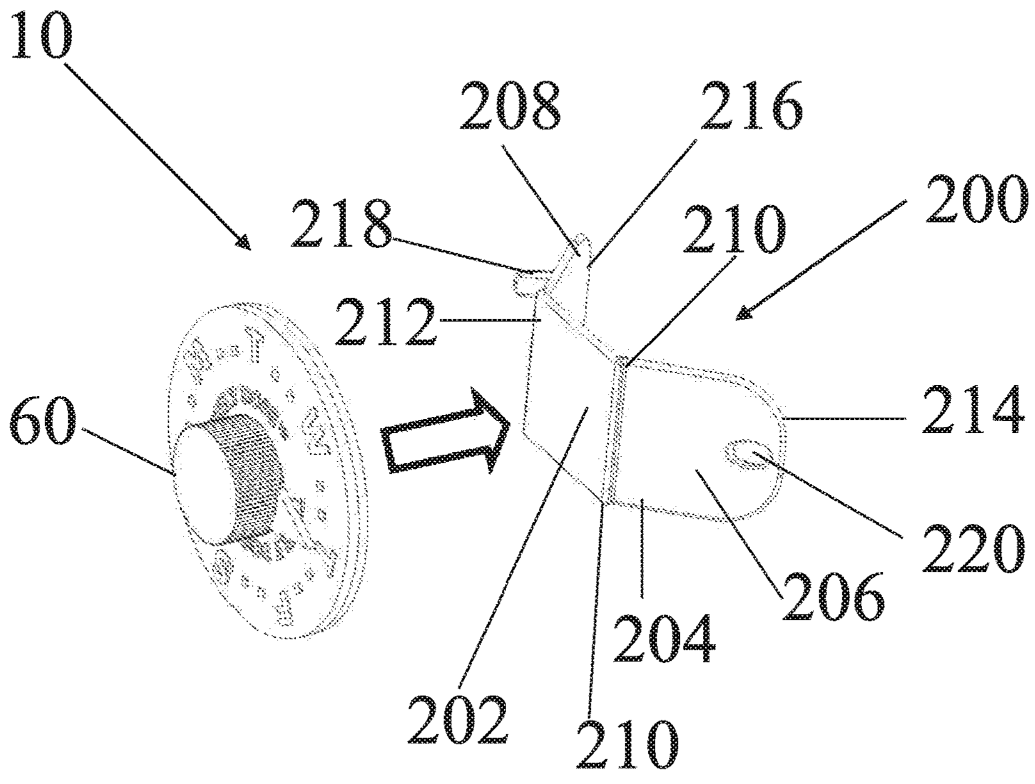
FIG. 10 is a perspective view illustrating a partially exploded view of the indicator device of FIG. 9.

As a third embodiment and referring to FIGS. 9 and 10, the dose indicator device 10 of the present invention can include a securing mechanism 200 for attaching the dose indicator device 100 to the sidewall 20 of a container 12. The securing mechanism 200 includes a flat surface 202 for receiving the second lower surface 48 of the base disk 40 of the dose indicator device 10 and a securing strap 204 for securing the dose indicator device 10 to the sidewall 20 of the container 12. As illustrated in the drawings, the securing strap 204 can be a two piece flexible strap, typically made of plastic or rubber, having two wrap around sections 206, 208 for frictionally securing the dose indicator device 10 to the sidewall 20 of the container 12. Each of the sections 206, 208 of the flexible securing strap 204 has a first proximal end 210, 212 connected to the flat surface of the securing strap and a distal ends 214, 216. As illustrated in FIG. 10, the distal ends 214, 216 include an interacting locking mechanism to secure the dose indicator device 10 to the sidewall 20 of the container 12. The locking mechanism includes an extended securing post 218 at distal end 216 and a co-acting opening 220 at distal end 214 for receiving the securing post 218. Other closure mechanisms, which are well known to the art, are also contemplated such as VELCRO® closures, clips, and the like. In addition the securing mechanism 200 may be a one-piece flexible strap for frictionally securing the dose indicator device 10 to the sidewall 20 of the container 12 as illustrated in FIG. 9.

The indicator device 10 can economically be affixed on disposable bottles or boxes and offered by pharmacies as an option to the consumer. All the pharmacy has to do is affix a self-adhesive label to the indicator device 10 and write on the dial as needed. In addition to its preferred use as a reminder device on medicine containers, the indicator device 10 has multiple other uses. For example, the device 10 can be placed on a furnace to indicate when a furnace filter must be replaced. In this case, the indicia 54 will be adapted to months of the year rather than hour segments during the day. Further, the indicator device 10 can be affixed to pet collars to indicate dosage requirements relating to flea and tick treatment and the like.

In addition, the indicator device 10 may come in different colors which can advantageously provide the user with another ready alert to indicate which pills are associated with a specific indicator device thereby discouraging the possibility of mixing medications and times.

Once the indicator device 10 is applied or installed on the container 12 or container cap 14, the rotating reminder dial 60 can be rotated to point to and designate a scheduled event when medication must be taken by the patient or to designate when the last dose of medication was administered. If medication is taken several times a day, the user-patient will probably want to set the dial 60 to show when the medication must be taken next. If the medication is only taken once daily, the dial 60 can be rotated to show when the medication was last taken.

By installing or applying an indicator device 60 to each container 12, the user can then easily coordinate the different schedules necessary for each medication dosage.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

BIBLIOGRAPHY

Basca, Belinda, 2008, "The Elderly and Prescription Drug Misuse and Abuse, Prevention Tactics (http://www.cars-rp.org/publications/Prevention%20Tactics/PT09.02.08.pdf)

What is claimed is:

1. A dose indicator device for attachment to a container cap on a container, comprising:

a. a base disk having a first upper surface and a second lower surface where in the first upper surface includes a center mount axle extending from center of the first upper surface of the base disk, wherein the center mount axle includes a shaft and a head and wherein a circumference of the head is larger than a circumference of the shaft, wherein the first upper surface supports an overlay plate with a center-spaced opening placed over the base disk such that the opening is placed over the center mount axle, wherein the overlay plate displays dose indicia for indicating time and the second lower surface of the base disk contains an adhesive, magnet base, or hook-and-loop fastener material which allows the base disk to be attached to a surface;

b. a reminder dial rotatably positioned at the center of the base disk by means of the center mount axle and extending outwardly toward the dose indicia for indicating time; and c. a second pointer directly attached to the base disk for designating a second date/time of interest.

2. The dose indicator device of claim 1 wherein the container is a medicine container.

3. The dose indicator device of claim 1 wherein the indicia includes a first set of indicia for the seven days of a week spaced circumferentially around the perimeter of the overlay plate, and a second set of indicia for a number of ingested doses of medication are spaced evenly between each indicator of the first set.

4. The dose indicator device of claim 1 wherein the dose indicator device is releasably affixed to the container cap.

5. The dose indicator device of claim 1 wherein the dose indicator device is permanently affixed to the container cap.

6. The dose indicator device of claim 1 wherein the container includes an open, upper first end, a closed, bottom second end and cylindrical sidewalls, wherein the first end includes a mechanism for closing the container cap onto the container and wherein the bottom end is flat for allowing the container to stand in an upright position.

7. The dose indicator device of claim 6 wherein the container cap includes a top surface with a circular side wall and a container closure mechanism located on the interior of the side wall.

8. The dose indicator device of claim 1 wherein the reminder dial comprises a first top end, a second bottom end and a generally circular wall disposed therebetween, wherein the second bottom end includes a cylindrical aperture for rotatably receiving the center mount axle of the base disk, wherein the aperture includes an internal ring approximately midway up the aperture for retaining the head of the center mount axle when the reminder dial is press fit onto the center mount axle.

9. The dose indicator device of claim 1 wherein the first top end of the reminder dial is blank to receive writings.

10. The dose indicator device of claim 1 wherein the reminder dial includes a pointer to indicate the direction pointed and to work with the indicia in order to designate the medication time.

11. The dose indicator device of claim 1 wherein the base disk contains a hook-and-loop fastener material.

12. The dose indicator device of claim 1 wherein the base disk contains a magnet base.

13. The dose indicator device of claim 1 further comprising a rotating indicia plate with a center-spaced opening placed over the base disk such that the opening is placed over the axle, wherein the first upper surface supports the rotating indicia plate, wherein the reminder dial is fitted onto the base disk.

14. The dose indicator device of claim 1 wherein the second pointer is adhered to the base disk.

15. The dose indicator device of claim 1 wherein the second pointer is formed as part of the base disk.

16. A container cap for attachment to a container, the container cap including a dose indicator device, the container cap comprising:

a. a first top surface with a circular side wall and a container closure mechanism located on the interior of the side wall, wherein the first top surface includes a center mount axle extending from center of the first top surface, wherein the center mount axle includes a shaft and a head and wherein a circumference of the head is larger than a circumference of the shaft, wherein the first upper surface supports an overlay plate with a center-spaced opening placed over the base disk such that the opening is placed over the center mount axle, wherein the overlay plate displays dose indicia for indicating time;

b. a reminder dial rotatably affixed to the center mount axle, wherein the reminder dial includes an indicator pointer extending outwardly toward the dose indicia for indicating time; and c. a second pointer directly attached to the base disk for designating a second date/time of interest.

* * * * *